US007952722B2

(12) United States Patent
Chan et al.

(10) Patent No.: US 7,952,722 B2
(45) Date of Patent: May 31, 2011

(54) OPTICAL IMAGE MEASUREMENT DEVICE

(75) Inventors: Kinpui Chan, Ridgewood, NJ (US);
Masahiro Akiba, Fort Lee, NJ (US);
Yasufumi Fukuma, Fort Lee, NJ (US)

(73) Assignee: Kabushiki Kaisha Topcon, Itabashi-ku (JP)

( * ) Notice: Subject to any disclaimer, the term of this patent is extended or adjusted under 35 U.S.C. 154(b) by 291 days.

(21) Appl. No.: 11/954,302

(22) Filed: Dec. 12, 2007

(65) Prior Publication Data

US 2009/0153876 A1 Jun. 18, 2009

(51) Int. Cl.
*G01B 11/02* (2006.01)
*G01B 9/02* (2006.01)

(52) U.S. Cl. ........................ 356/497; 356/492

(58) Field of Classification Search ............... 356/479, 356/491–493, 495, 497; 359/200, 205, 209, 359/210

See application file for complete search history.

(56) References Cited

U.S. PATENT DOCUMENTS

| 5,847,827 | A * | 12/1998 | Fercher | 356/493 |
| 7,643,154 | B2 * | 1/2010 | Kikawa et al. | 356/497 |
| 2006/0082781 | A1 * | 4/2006 | Chan et al. | 356/495 |
| 2008/0117432 | A1 * | 5/2008 | Reimer et al. | 356/511 |

FOREIGN PATENT DOCUMENTS

| JP | 2006-116028 | 5/2006 |
| JP | 2006-153838 | 6/2006 |

* cited by examiner

*Primary Examiner* — Michael A Lyons
(74) *Attorney, Agent, or Firm* — Edwards Angell Palmer & Dodge LLP (57) ABSTRACT

An optical image measurement device comprises: a light source configured to output a light having low temporal coherence and low spatial coherence; an optical system configured to split the light into a signal light and a reference light and superimpose the signal light having passed through a measured object and the reference light, thereby generating an interference light; a light receiver configured to receive the interference light and output an electric signal; and a forming part configured to form an image of the measured object based on the electric signal, wherein: the light receiver has a light receiving face on which a plurality of light receiving elements are arranged 2-dimensionally; and the optical system projects the interference light onto the light receiving face so that a size of the spatial coherent region of the interference light becomes equal to or larger than a size of the light receiving element.

14 Claims, 5 Drawing Sheets

OPTICAL IMAGE MEASUREMENT DEVICE

BACKGROUND OF THE INVENTION

1. Field of the Invention

The present invention relates to an optical image measurement device for forming an image of a measured object by using the OCT technology.

2. Description of the Related Art

Recently, attention has focused on an optical image measurement device that forms an image of a measured object by using the OCT (Optical Coherence Tomography) technology. The optical image measurement device splits a low-coherence light into two (lights), and applies one (signal light) of the two to the measured object and the other (reference light) to a reference object. Then, it superimposes the signal light having passed through the measured object and the reference light having passed through the reference object to generate and detect an interference light, and analyzes the detection result to form an image of the measured object (e.g., see Japanese Unexamined Patent Application Publications JP-A 2006-153838 and JP-A 2006-116028).

Since such an optical image measurement device uses an interferometer, it becomes possible to measure with favorable resolving power and sensitivity as compared with other measuring methods. Moreover, since the optical image measurement device performs measurement by using a weak light, there is an advantage of higher safety (less invasive) for a living body.

The optical image measurement device disclosed in JP-A 2006-153838 is called a full-field type or an en-face type. This type of optical image measurement device applies a signal light having a specific beam diameter to a measured object, and thereby forms a tomographic image of a cross section orthogonal to the travel direction of the signal light.

Further, the optical image measurement device disclosed in JP-A 2006-116028 is called a Fourier domain type. This type of optical image measurement device scans an application position of a signal light on a measured object, and thereby forms a depth-wise image at each application position. Then, the optical image measurement device arranges a plurality of depth-wise images, and thereby forms a tomographic image of a cross-section extending in the travel direction (depth direction) of the signal light.

The Fourier domain type uses a coherent light that is temporally low and spatially high. The low temporal coherence secures the resolving power in the depth direction. Moreover, the high spatial coherence causes speckle noise, and limits the resolving power in the direction (horizontal direction) orthogonal to depth direction.

On the other hand, since the full-field type can use a light with low coherence in terms of time and space, it is possible to acquire an image with excellent resolving power in both the depth direction and horizontal direction.

As mentioned above, for an optical image measurement device, it is very important to consider light coherence, in specific, spatial coherence. However, for a conventional optical image measurement device, no efforts have been made to improve measurement with the main aim of spatial coherence.

SUMMARY OF THE INVENTION

The present invention has been made based on the aforementioned aspects, and an object of the present invention is to provide an optical image measurement device that enables improvement of measurement sensitivity by considering spatial coherence of light.

In order to achieve the above object, in a first aspect of the present invention, an optical image measurement device comprises: a light source configured to output a light having low temporal coherence and low spatial coherence; an optical system configured to split the light into a signal light and a reference light and superimpose the signal light having passed through a measured object and the reference light having passed through a reference object, thereby generating an interference light; a light receiver configured to receive the interference light and output an electric signal; and a forming part configured to form an image of the measured object based on the electric signal, wherein: the light receiver has a light receiving face on which a plurality of light receiving elements are arranged 2-dimensionally; and the optical system projects the interference light onto the light receiving face so that a size of the spatial coherent region of the interference light becomes equal to or larger than a size of the light receiving element on the light receiving face.

In a second aspect of the present invention, an optical image measurement device comprises: a light source configured to output a light having low temporal coherence and low spatial coherence; an optical system configured to split the light into a signal light and a reference light and superimpose the signal light having passed through a measured object and the reference light having passed through the reference object, thereby generating an interference light; a light receiver configured to receive the interference light and output an electric signal; and a forming part configured to form an image of the measured object based on the electric signal, wherein: the light receiver has a light receiving face on which a plurality of light receiving elements are arranged 2-dimensionally; and the optical system projects the interference light onto the light receiving face so that a size of the spatial coherent region of the interference light becomes substantially equal to a size of the light receiving element on the light receiving face.

The optical image measurement device according to the present invention outputs a light having low temporal coherence and low spatial coherence, splits the light into a signal light and a reference light, superimposes the signal light having passed through a measured object and the reference light having passed through a reference object to generate and receive an interference light, and forms an image of the measured object based on the light receiving result. The light receiver configured to receive the interference light has a light receiving face on which a plurality of light receiving elements are arranged 2-dimensionally. The optical system of the optical image measurement device projects the interference light onto the light receiving face so that the size of the spatially coherent region of the interference light becomes equal to or larger than the size of the light receiving element on the light receiving face. According to such an optical image measurement device, it is possible to improve the measurement sensitivity.

Further, in another aspect of the present invention, the optical image measurement device outputs a light having low temporal coherence and low spatial coherence, splits the light into a signal light and a reference light, superimposes the signal light having passed through the measured object and the reference light having passed through a reference object to generate and receive an interference light, and forms an image of a measured object based on the light receiving result. The light receiver configured to receive the interference light has a light receiving face on which a plurality of light receiving elements are arranged 2-dimensionally. The optical system of the optical image measurement device projects the interference light onto the light receiving face so that the size of the spatial coherent region of the interference light becomes substantially equal to the size of the light receiving element on the light receiving face. According to such an optical image measurement device, it is possible to improve the measurement sensitivity without narrowing a measurement range.

DETAILED DESCRIPTION OF THE PREFERRED EMBODIMENT

Figure 1:
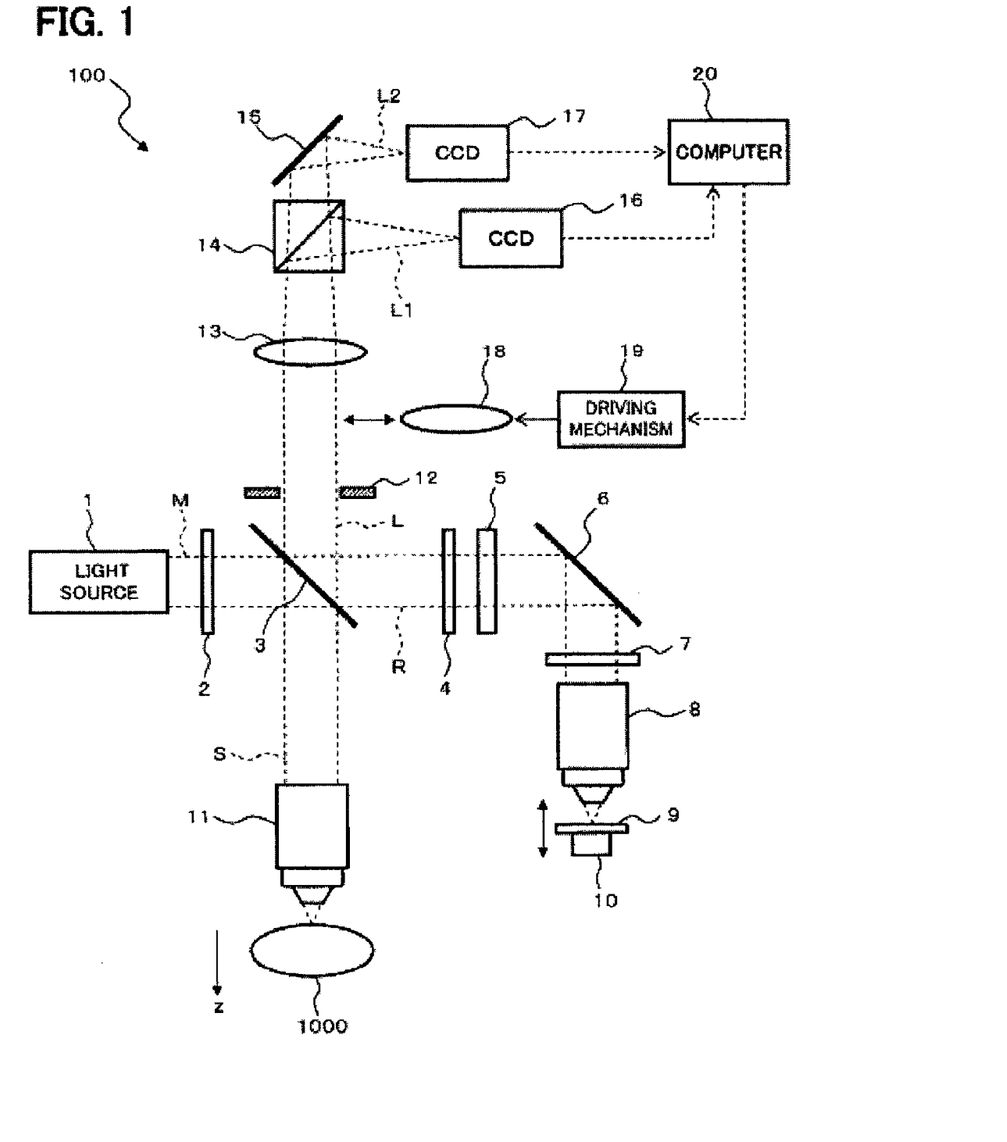
FIG. 1 is a schematic configuration view showing an example of the overall configuration of an embodiment of the optical image measurement device according to the present invention.

An embodiment of the optical image measurement device according to the present invention will be described in detail referring to the drawings.
[Configuration]
FIG. 1 shows an example of the configuration of the optical image measurement device according to the present embodiment. An optical image measurement device 100 is a full-field type OCT device. The optical image measurement device 100 applies a signal light S having a specific beam diameter onto a measured object 1000, and detects an interference light L (having a specific beam diameter) generated by superimposing the signal light S and the reference light R, with a 2-dimensional light sensor array. Furthermore, the optical image measurement device 100 analyzes the detection result of the interference light L, and thereby forms a 2-dimensional image of the region of the measured object 1000 depending on the beam diameter of the signal light S.

The measured object 1000 is placed in the condition appropriate for measurement. For example, in a case where the measured object 1000 is a living body, in order to minimize a change of a refractive index at the boundary, it is possible to apply jelly, liquid or the like to the living body. In a case where the measured object 1000 is not a living body, in order to minimize a change of a refractive index at the boundary, it is possible to measure by immersing the measured object 1000 in liquid.

The optical image measurement device 100 comprises a light source 1. The light source 1 outputs a light (low-coherence light) M with both the low temporal coherence and low spatial coherence. The low-coherence light M is, for example, a non-polarized broadband light.

The degree of temporal coherence and spatial coherence of the low-coherence light M may be low enough as far as imaging of the measured object 1000 can be done based on the measuring principle according to the present embodiment. Moreover, the lowness of temporal coherence and spatial coherence of the low-coherence light M can be set appropriately in consideration of the resolving power or the like.

The light source 1 can be configured so as to include a light source device that outputs a light, an optical fiber bundle that guides the outputted light, and a Kohler illumination optical system for uniformly illuminating the application field of the outputted light, which are not illustrated in the drawings.

Further, the light source 1 may also be provided with an aperture member (illumination aperture) configured to shield part of the outputted light and thereby determine the beam diameter of the outputted light. For example, the illumination aperture is configured so as to change the beam diameter of the outputted light by changing the size of a light transmitting region that transmits a light, namely, by changing an aperture value. With the aforementioned configuration, the low-coherence light M outputted from the light source 1 becomes a light flux having a specific beam diameter. The illumination aperture can be provided at any position in the optical path of the low-coherence light M.

The light source 1 includes a heat light source (light source based on blackbody radiation) such as an incandescent lamp, a halogen lamp and a xenon lamp. The light source 1 may be one that outputs a randomly polarized broadband light. Here, "non-polarized light" refers to a condition of polarization including a linearly polarized light, a circularly polarized light, and an elliptically polarized light. Moreover, "randomly polarized light" refers to a condition of polarization having two linearly polarized components that are orthogonal to each other, in which the power of each of the linearly polarized components randomly varies with time (e.g., see Japanese Unexamined Patent Application Publication JP-A H7-92656). Although only the case of the non-polarized light will be described below in detail, it is possible to achieve the same actions and advantageous effects with the same configuration, also in the case of randomly polarized light. The light source 1 is composed of any light source that outputs a light of low temporal coherent and low spatial coherent.

The low-coherence light M (non-polarized broadband light) contains lights of various bands. A filter 2 is a filter configured to transmit only a specific band of the low-coherence light M. The band passing through the filter 2 can be determined by resolving power, measurement depth, or the like. For example, it is set to a band with a central wavelength of about 760 nm and a wavelength width of about 100 nm. In this case, it is possible to acquire an image with a resolving power of about 2 μm in each of the depth-wise direction (z direction shown in FIG. 1) and the orthogonal direction (horizontal direction) of the measured object 1000. Here, the light having passed through the filter 2 will also be referred to the low-coherence light M.

The low-coherence light M having passed through the filter 2 is split into two by the beam splitter 3. In other words, the reflected light by the beam splitter 3 forms the signal light S, and the light having passed through the beam splitter 3 forms the reference light R. The beam splitter 3 is composed of, for example, a half mirror.

The signal light S is focused by an objective lens 11 onto the measured object 1000 while maintaining a non-polarized state. At this moment, the signal light S is applied to the measured object 1000 with a specific beam diameter. The light reflected or scattered on the surface or inside of the measured object 1000 returns to the beam splitter 3 via the objective lens 11.

On the other hand, the non-polarized reference light R generated by the beam splitter 3 passes through a wavelength plate (λ/4 plate) 4 and a polarizing plate 5, and is reflected by a reflection mirror 6. Furthermore, the reference light R passes through a glass plate 7, and is focused on the reflecting face of a reference mirror 9 by an objective lens 8. The reference light R reflected by the reference mirror 9 returns to the beam splitter 3 via the same optical path, inversely.

At this moment, the initially non-polarized reference light R is converted into a circularly polarized light after passing through the wavelength plate 4 and the polarizing plate 5 twice. The glass plate 7 is a dispersion correction optical element that minimizes effects of dispersion that occurs in the optical paths of the signal light S and the reference light R (both arms of the interferometer).

The reference mirror 9 can be moved by a reference-mirror moving mechanism 10 in the travel direction of the reference light R, that is, the orthogonal direction to the reflecting face of the reference mirror 9 (direction of arrow directing both sides in FIG. 1). The reference-mirror moving mechanism 10 comprises a driver such as a piezoelectric element. The reference-mirror moving mechanism 10 is an example of the "moving part" according to the present invention.

By thus moving the reference mirror 9, a difference in optical path length between the signal light S and the reference light R is changed. Here, the optical path length of the signal light S refers to a reciprocation distance between the beam splitter 3 and the surface of the measured object 1000. Moreover, the optical path length of the reference light R refers to a reciprocation distance between the beam splitter 3 and the reflecting face of the reference mirror 9. By changing the difference in optical path length between the signal light S and the reference light R, it is possible to selectively acquire images at various depth positions of the measured object 1000.

Although the difference in optical path length is changed by changing the optical path length of the reference light R in this embodiment, it is also possible to configure so as to change the difference in optical path length by changing the optical path of the signal light S. In this case, a mechanism that changes the interval between the device optical system and the measured object 1000. As such a mechanism, it is possible to apply a stage for moving the device optical system in the z direction, a stage for moving the measured object 1000 in the z direction, and the like.

The signal light S having passed through the measured object 1000 and the reference light R having passed through the reference mirror 9 are superimposed by the beam splitter 3 to generate the interference light L. The interference light L contains the S polarization components and the P polarization components.

The interference light L generated by the beam splitter 3 passes through the aperture 12 and becomes a convergent light by the imaging lens (group) 13. The aperture 12 limits the beam diameter of the interference light L by shielding part of the interference light L. The aperture 12 is configured so as to change the beam diameter of the interference light L by, for example, changing the size of the light transmitting region to transmit the light (that is, by changing the aperture value).

The interference light L having become a convergent light is split into two by the polarization beam splitter 14. In other words, S polarization component L1 of the interference light L is reflected by the polarization beam splitter 14, and P polarization component L2 passes through the polarization beam splitter 14. The polarization beam splitter 14 is an example of the "splitter" according to the present invention.

The S polarization component L1 is projected onto a CCD (Charge-Coupled Device, image sensor) 16. On the other hand, the P polarization component L2 is reflected by a reflection mirror 15, and projected onto a CCD (image sensor) 17.

On the light receiving face of each of the CCDs 16 and 17, a plurality of light receiving elements (CCD elements) are arranged 2-dimensionally. The S polarization component L1 and the P polarization component L2 are projected onto the light receiving faces of the CCDs 16 and 17, respectively, with a specific beam diameter (to be described).

The CCD 16 receives the S polarization component L1, generates an electric signal, and sends the electric signal to a computer 20. The CCD 17 receives the P polarization component L2, generates an electric signal, and sends the electric signal to the computer 20. The CCD 16 and 17 is an example of the "light receiver" according to the present invention.

The light receiver is not limited to a CCD. Any light-receiving devices such as a CMOS (Complementary Metal-Oxide Semiconductor, image sensor) can be applied as the light receiver for detecting the light, performing photoelectric conversion, and generating an electric signal.

The reference light R is a circularly-polarized light, and the signal light S is a non-polarized light (or a randomly-polarized light), both of which are used for generating the interference light L. Therefore, the S polarization component L1 and the P polarization component L2 have a phase difference of 90° (π/2). Accordingly, an electric signal $C_A$ outputted from the CCD 16 and an electric signal $C_B$ outputted from the CCD 17 have a phase difference of 90°. This can be expressed by the following formula.

[Formula 1]

$$C_A(x,y)=I_s(x,y)+I_r(x,y)+\sqrt{I_s(x,y)I_r(x,y)}\cos(\Delta\phi(x,y)) \quad (1)$$

$$C_B(x,y)=I_s(x,y)+I_r(x,y)+\sqrt{I_s(x,y)I_r(x,y)}\sin(\Delta\phi(x,y)) \quad (2)$$

Wherein, $I_s$ (x, y) represents the intensity of the signal light S, and $I_r$ (x, y) represents the intensity of the reference light R. φ(x, y) represents an initial phase difference (here, φ is phi). Each of the electric signals $C_A$ and $C_B$ contains a background light component $I_s$ (x, y)+$I_r$ (x, y). The background light component is also referred to as a noninterference component or direct current component. Furthermore, the electric signal $C_A$ contains an interference component composed of a cos component, and the electric signal $C_B$ contains an interference component composed of a sin component.

As understood from the formula (1) and (2), each of the electric signals $C_A$ and $C_B$ contains only space (the x and y directions orthogonal to the z direction) as a variable, and does not contain time as a variable. In other words, an interference signal relating to the present embodiment contains only a spatial change.

The optical image measurement device 100 is equipped with a variable magnifying lens 18. The variable magnifying lens 18 is inserted in and retracted from the optical path of the interference light L by a driving mechanism 19. The driving mechanism 19 is configured to include an actuator such as a motor and a solenoid coil.

The variable magnifying lens 18 may be a single lens, or may be composed of a plurality of lenses with different magnifications (powers). In the former case, the driving mechanism 19 performs an operation of inserting the single lens into the optical path and an operation of retracting it from the optical path.

On the other hand, in the latter case, a plurality of lenses are mounted on a disc turret or the like. For example, a plurality of lenses are arranged along the circumferential direction of the turret. The driving mechanism 19 performs so as to rotate the turret around the center position of the disc shape (the axis is placed in the retracted position from the optical path) and thereby selectively arrange the plurality of lenses in the optical path. Thus, it is possible to make various magnifications act on the interference light L selectively. In a case where the lens is not made to act on by the interference light L, the driving mechanism 19 retracts the turret from the optical path. Moreover, it is also possible to configure so that the turret is provided with an opening part (may be a light transmitting region that does not change the magnification) and, when the lens is not made to act on the interference light L, the driving mechanism 19 rotates the turret to situate the opening part in the optical path.

Further, the variable magnifying lens 18 and the driving mechanism 19 may have a known configuration that enables continuous change of the magnification (power).

By installing such a variable magnifying lens 18, it becomes possible to change the beam diameter of the S polarization component L1 projected onto the light receiving face of the CCD 16 and the beam diameter of the P polarization component L2 projected onto the CCD 17. The beam diameter depends on the condition of the illumination aperture, the aperture 12 or the like mentioned before.

In the present embodiment, the variable magnifying lens 18 is inserted between the aperture 12 and the imaging lens 13. However, the insertion position of the variable magnifying lens 18 is not limited to that position and may be any position in the optical path of the interference light L.

Further, it is also possible to configure so that a variable magnifying lens can be inserted in and retracted from each of the optical paths of the S polarization component L1 and the P polarization component L2.

[Configuration of Control System]

Figure 2:
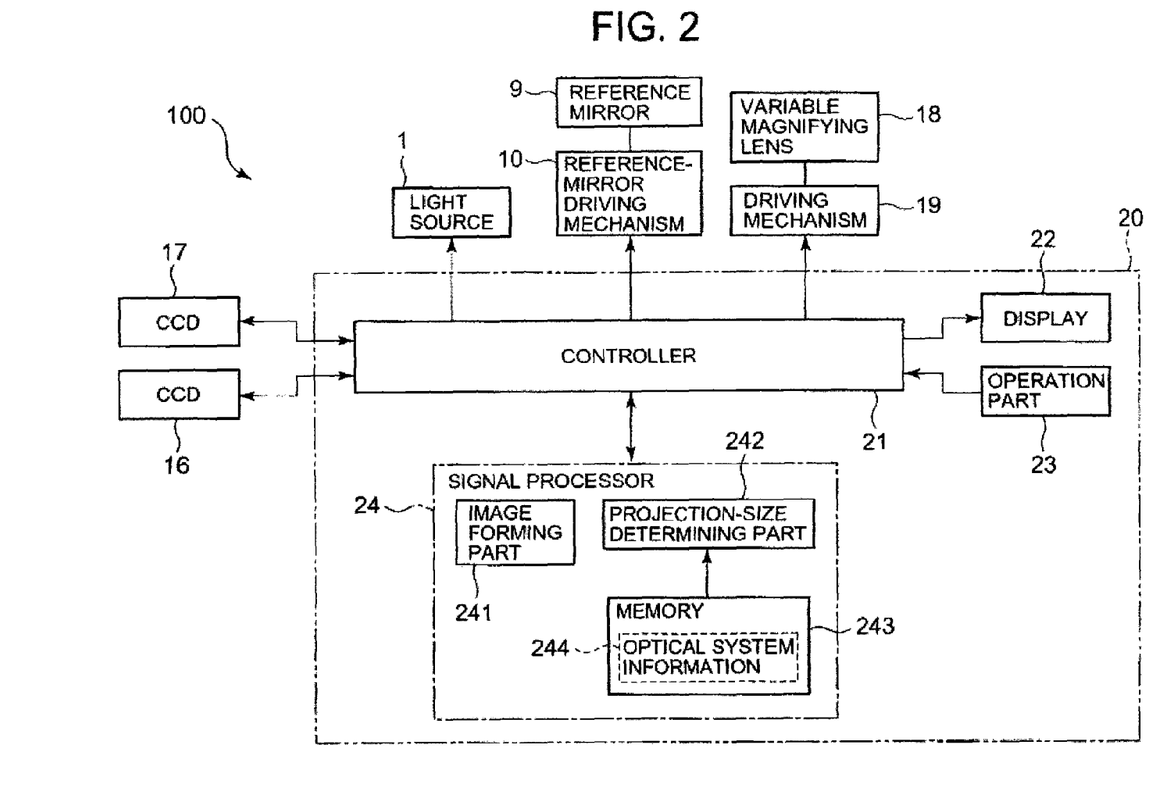
FIG. 2 is a schematic block diagram showing an example of the control system configuration of an embodiment of the optical image measurement device according to the present invention.

The configuration of a control system of the optical image measurement device 100 will be described below. FIG. 2 shows an example of the configuration of the control system of the optical image measurement device 100.

The computer 20 comprises a controller 21, a display 22, an operation part 23, and a signal processor 24. The controller 21 and the signal processor 24 function as an example of the "controller" according to the present invention.

(Controller)

The controller 21 controls the respective parts of the optical image measurement device 100. For example, the controller 21 executes control of turning-on/off of the light source 1, control of the reference-mirror moving mechanism 10, control of the driving mechanism 19, control of operation of the CCDs 16 and 17 (e.g., control of exposure time), and control of the display 22.

The controller 21 includes a microprocessor such as a CPU (Central Processing Unit). Moreover, the controller 21 includes a memory device such as a RAM (Random Access Memory), a ROM (Read Only Memory), and a hard disk drive. A computer program for device control (not shown) is prestored in the hard disk drive. The microprocessor operates in accordance with the computer program, whereby the controller 21 executes the various controls as mentioned above.

Further, the controller 21 may include a communication device for performing data communication with an external device. The communication device may be a LAN (Local Area Network) card or a modem. Thus, the controller 21 can obtain various kinds of information from an external database, and register the information into the database. Furthermore, the controller 21 can obtain information from an ophthalmic device such as an examination system, or send the information to the ophthalmic device.

(Display)

The display 22 is controlled by the controller 21 to display various kinds of information. The display 22 includes any display device such as an LCD (Liquid Crystal Display) and a CRT (Cathode Ray Tube) display.

(Operation Part)

The operation part 23 is used by the operator to operate the optical image measurement device 100 and input various kinds of information. The operation part 23 includes any operation device and input device such as a mouse, a keyboard, a joystick, a trackball and a dedicated control panel.

(Signal Processor)

The signal processor 24 processes various signals. The signal processor 24 includes a microprocessor like a CPU, a RAM, a ROM and a hard disk drive. The signal processor 24 is provided with an image forming part 241, a projection-size determining part 242, and a memory 243.

(Image Forming Part)

The image forming part 241 forms an image of the measured object 1000 based on the electric signals $C_A$ and $C_B$ outputted from the CCDs 16 and 17. In particular, the image forming part 241 forms a tomographic image of the measured object 1000 having a cross section of the orthogonal face to the depth-wise (travel direction of the signal light S) of the measured object 1000.

Further, the image forming part 241 can form a 3-dimensional image of the measured object 1000 based on tomographic images at a plurality of depth-wise positions of the measured object 1000. The 3-dimensional image is an image that represents a 3-dimensional pattern (or function) of the measured object 1000. The 3-dimensional image (image data thereof) may be stack data or volume data. The stack data is an image that can be obtained by arranging a plurality of tomographic images (2-dimensional images) by using a single 3-dimensional coordinate system. The volume data is an image that can be obtained by interpolating images between adjacent tomographic images and thereby forming a voxel (3-dimensional pixel). The volume data is also referred to as voxel data.

Further, the image forming part 241 forms a depth-wise tomographic image of the measured object 1000. The tomographic image can be formed for any cross section of the 3-dimensional image.

An example of processes that the image forming part 241 performs will be described later. The image forming part 241 is an example of the "forming part" according to the present invention.

(Projection-Size Determining Part)

The projection-size determining part 242 determines the size of the spatial coherent region of the interference light L (polarization components L1 and L2) projected onto the respective CCDs 16 and 17. Below, the spatial coherence region will be described.

As mentioned above, the interference light L is generated based on the low-coherence light M with low temporal coherence and low spatial coherence. Accordingly, in the interference light L, the lowness of temporal coherence and spatial coherence is maintained.

The optical image measurement device 100, which is a full-field OCT (Optical Coherence Tomography) device as mentioned above, is characterized by use of a light with low spatial coherence as compared with other types. In general, spatial coherence represents the easiness of interference of a light at a spatially apart position. The lowness of the spatial coherence means that a spatial region in which light can interfere (referred to as a spatial coherent region) is small. Therefore, the size of the spatial coherent region of the interference light L (may be any factor that represents the size of the spatial coherent region such as length, area, diameter, circumferential length) is a factor that affects the image resolving power in the horizontal direction.

Figure 3:
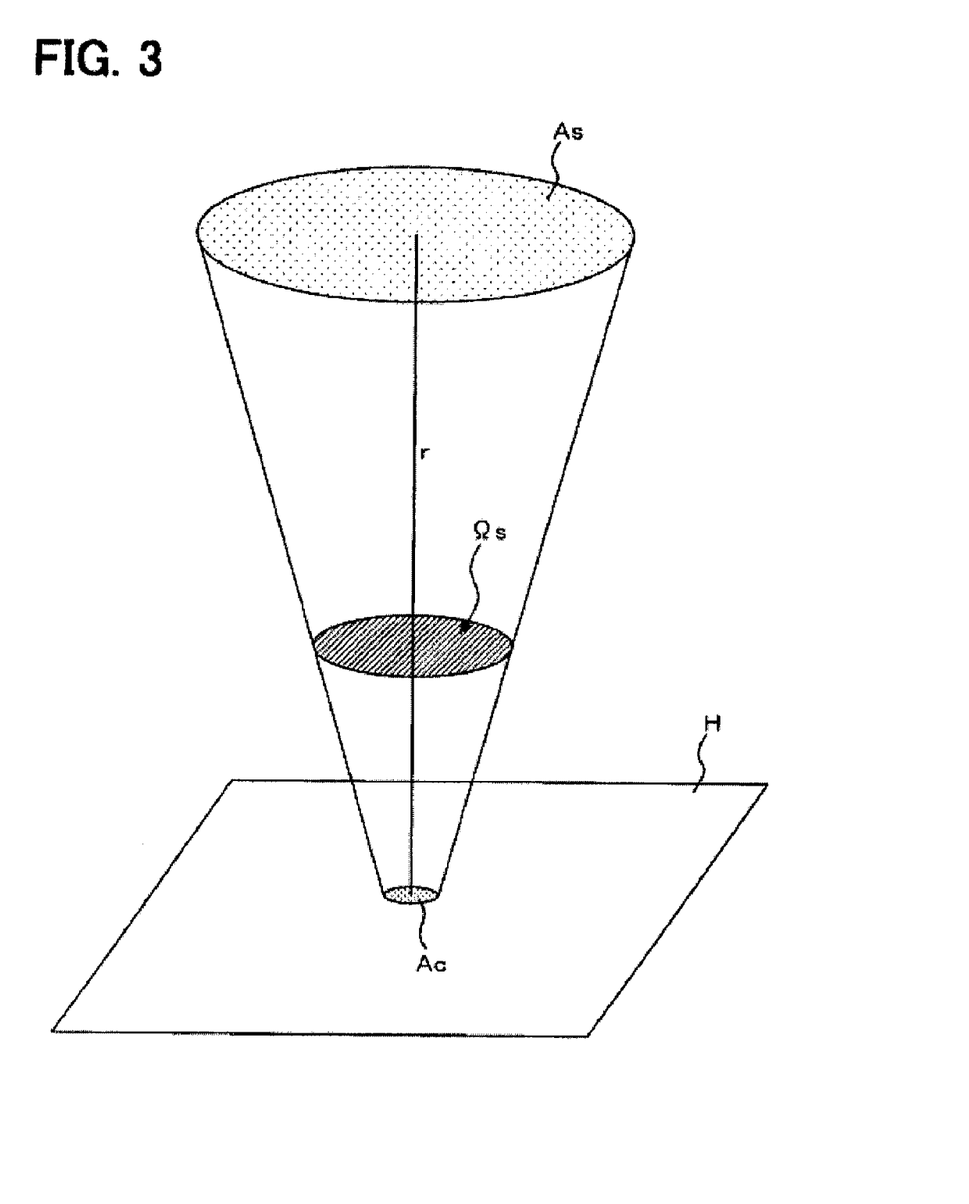
FIG. 3 is a schematic illustration view for explaining a spatial coherent region.

In general, assuming the area of a cross section of an incoherent light with uniform brightness is As, the area of a spatial coherent region on a face (projection face) H on which the light is projected is Ac, a solid angle of the light projected onto the projection face H is $\Omega s$, a distance between the cross-section and the projection surface H is r, and a wavelength of the light is λ, the following relation is established by the Van Cittert-Zernike theorem (see FIG. 3).

[Formula 2]

$$Ac = \frac{\lambda^2 r^2}{As} = \frac{\lambda^2}{\Omega s} \quad (3)$$

Furthermore, assuming the spatial coherent length of the light (spatial distance in which light can interfere) is dc, the effective area of the objective lens 8, 11 corresponds to the optical image measurement device 100. Therefore, the spatial coherent length dc can be obtained from the following formula.

[Formula 3]

$$dc = 0.64 \times \frac{\lambda}{NA} \quad (4)$$

Wherein, NA represents the number of apertures (numerical aperture) of the objective lenses 8, 11. As such, according to the optical image measurement device 100, spatial coherence is as low as the resolution capability of the objective lenses 8, 11 (≈0.6 λ/NA). For example, in the case of NA=0.2, the spatial coherence length dc becomes about 2 μm.

As understood from the aforementioned descriptions, the size (e.g., spatial coherent length dc) of the spatial coherent region of the interference light L (polarization components L1 and L2) projected onto the CCDs 16 and 17 depends on the optical system configuration of the optical image measurement device 100. In other words, if the optical system configuration including the lens power, aperture value, and an arrangement interval of the optical element is known, it is possible to obtain the size of the spatial coherent region of the polarization components L1 and L2 on the light receiving face of the CCD 16 and 17.

Information (optical system information 244) on the optical system configuration of the optical image measurement device 100 is preliminarily stored in the memory 243. The optical system information 244 contains all information referred to in order to calculate the size of the spatial coherent region of the polarization components L1 and L2 projected onto the CCD 16 and 17. In a case where the variable magnifying lens 18 is provided with a plurality of magnifying lenses, the optical system information 244 contains the magnification (power) of each lens. Moreover, the optical system information 244 contains information that represents the size of the light receiving element arranged on the light receiving faces of the CCDs 16 and 17 (information representing the size of the light receiving elements, such as the area and diameter).

The projection-size determining part 242 refers to the optical system information 244, thereby calculating the size of the spatial coherent region of the polarization components L1 and L2 on the light receiving faces of the CCDs 16 and 17 for the polarization components L1 and L2 projected onto the CCDs 16 and 17. In the aforementioned calculation, the area of a spatial coherent region can be obtained. However, by assuming the shape of the spatial coherent region, it is possible to obtain the diameter and length as well.

In particular, the projection-size determining part 242 determines such a size of the spatial coherent region of the polarization components L1 and L2 that is equal to or larger than the size of the light receiving face of the CCDs 16 and 17. This process can be performed, for example, by setting the size of the spatial coherent region so as to be equal to or larger than the size of the light receiving element and obtaining the magnification of the variable magnifying lens 18 corresponding to that size.

[Operation Mode]

Figure 4:
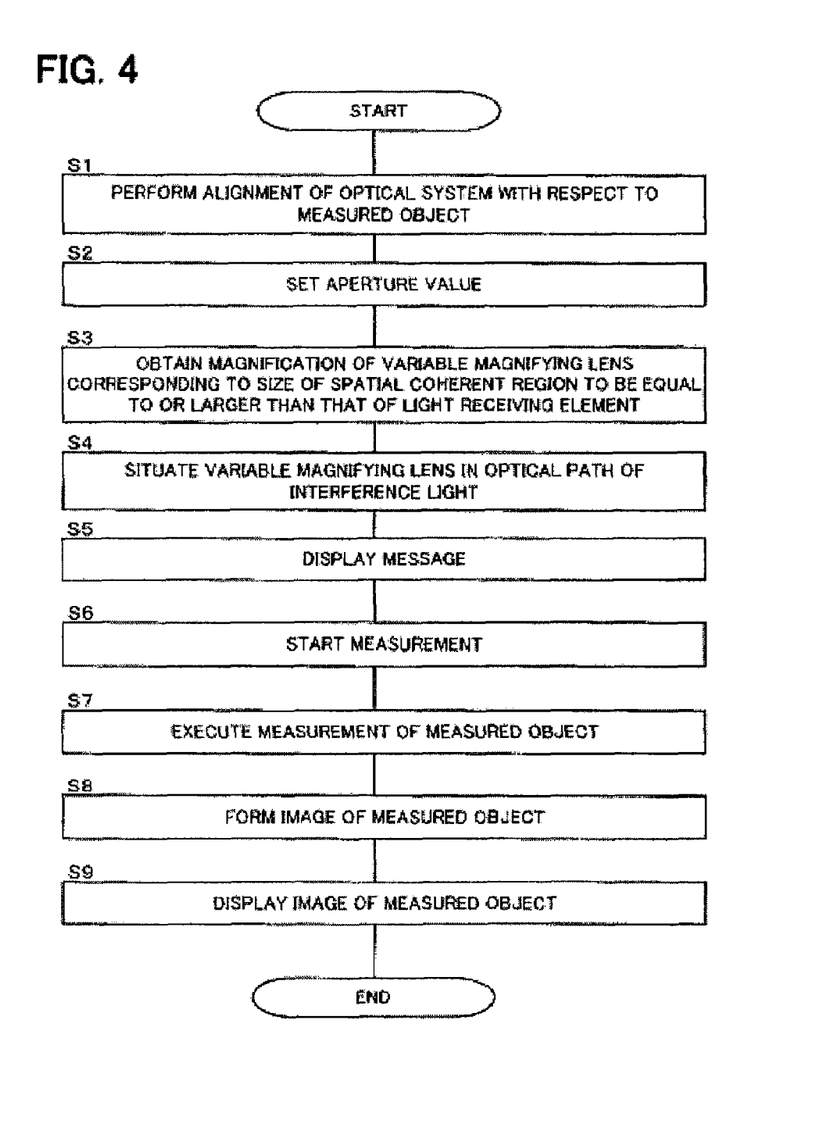
FIG. 4 is a flowchart showing an example of the operation mode of an embodiment of the optical image measurement device according to the present invention.

An operation mode of the optical image measurement device 100 will now be explained. A flowchart shown in FIG. 4 represents an example of the operation mode of the optical image measurement device 100.

First, the measured object 1000 is situated in a specific measuring position, and alignment (position-matching) of the optical system with respect to the measured object 1000 is performed (S1). As for the alignment, in the same manner as the conventional full-field OCT device, it is possible to adjust a relative position between the measured object 1000 and the optical system. At this moment, the position of the reference mirror 9 (measurement depth of the measured object 1000) is also set. The alignment may be performed manually by the operator. The optical image measurement device may be configured so that the alignment is performed automatically in the same manner as in other optical devices (a camera, an opthalmologic device, etc.). The controller 21 sends the alignment result (information that represents the condition of the optical system after alignment) to the signal processor 24.

Next, the aperture value of the illumination aperture (mentioned above) and/or the aperture 12 of the light source 1 is set (S2). Setting of the aperture value can be performed manually. Furthermore, it may be configured so that the aperture value is set automatically in the same manner as other optical devices (a camera, an opthalmologic device, etc.). The controller 21 sends the setting contents (aperture value information) in Step 2 to the signal processor 24.

Then, the projection-size determining part 242 obtains the magnification of the variable magnifying lens 18 corresponding to the size of the spatial coherent region to become equal to or larger than the size of the light receiving element based on the information from the controller 21 (Step 1, 2) and the optical system information 244 (S3). The signal processor 24 sends information on the obtained magnification of the variable magnifying lens 18 to the controller 21.

The controller 21 controls the driving mechanism 19 to situate the variable magnifying lens 18 with the magnification obtained in Step 3 in the optical path of the interference light L (S4). In this case, when the magnification obtained in Step 3 is 1, the controller 21 retracts the variable magnifying lens 18 from the optical path (or arranges the aforementioned opening part in the optical path).

After the above preparation is completed, the controller 21 controls the display 22 to display information indicating "ready to measure" (e.g., message) in the display 22. The operator confirms that this information is displayed, operates the operation part 23, and requests to start the measurement (S6).

When an operation to start measurement is done, the controller 21 controls the light source 1, the reference-mirror moving mechanism 10, the CCDs 16 and 17, and so on to execute the measurement (S7). The controller 21 receives electric signals output from the CCDs 16, 17 and sends them to the signal processor 24.

The image forming part 241 forms an image of the measured object 1000 based on these electric signals (S8). An example of an operation for forming the image will be described below.

When the operator requests to start a specific measurement using the operation part 23 (S6), the controller 21 causes the light source 1 to light on. In this operation mode, in the condition in which the light source 1 is turned on, a continuous low-coherence light M is outputted.

Next, the controller 21 controls the reference-mirror moving mechanism 10 to situate the reference mirror 9 at the first position. In this case, the optical path length (first optical path length) of the reference light R corresponds to the first depth position (z coordinate value) of the measured object 1000. The controller 21 controls the exposure time of each of the CCDs 16 and 17. The CCDs 16 and 17 output the interference light electric signals $C_A$ and $C_B$, respectively.

Then, the controller 21 controls the reference-mirror moving mechanism 10 so as to move the reference mirror 9 to the second position. In this case, the optical path length (second optical path length) of the reference light R corresponds to the second depth position of the measured object 1000. The controller 21 controls the exposure time of each CCD 16 and 17 to output a new electric signal $C_A'$ and $C_B'$.

Here, the first optical path length and the second optical path length are preliminarily set so that the electric signal $C_A$ and the electric signal $C_A'$ have a phase difference of 180° ($\pi$), and the electric signal $C_B$ and the electric signal $C_B'$ have a 180° ($\pi$) phase difference. Since the electric signals $C_A$ and $C_B$ have a 90° phase difference, it means that four electric signals $C_A$, $C_B$, $C_A'$, and $C_B'$ can be obtained by a 90° phase difference.

The image forming part 241 adds the electric signals $C_A$ and $C_A'$ (phase difference 180°) and divides the sum by 2, thereby calculating the background light component $I_s$ (x, y)+$I_r$ (x, y). The calculation may be performed by using the electric signals $C_B$ and $C_B'$ (phase difference 180°).

Furthermore, the image forming part 241 obtains the interference components (cos component, sin component) by subtracting the background light component $I_s$ (x, y)+$I_r$ (x, y) from each of the electric signals $C_A$ and $C_B$. Then, the image forming part 241 calculates the square sum of the interference components for the electric signals $C_A$ and $C_B$, thereby forming an image of the cross section in the x-y direction (horizontal direction). This calculation may be performed by using the electric signals $C_A'$ and $C_B'$ (phase difference 180°).

The controller 21 changes the optical path length of the reference light R and repeats the abovementioned processing, thereby sequentially forming the x-y cross-section image at various depth-wise positions of the measured object 1000.

In this process, the controller 21 controls the CCDs 16 and 17 so as to output an electric signal at a specific frame rate and at the same timing, and synchronizes this frame rate with the exposure timing of each of the CCDs 16 and 17, the timing for moving the reference mirror 9, and the timing for changing the optical path length of the reference light R.

At this moment, the exposure time of each of the CCDs 16 and 17 is set to be shorter than the frame rate. For example, it is possible to set the frame rate of the CCDs 16 and 17 to 30 f/s and the exposure time to about 30-50 μs.

Further, by using the low-coherence light M (generated by the filter 2) with a center wavelength of about 760 nm and a wavelength width of about 100 nm, it is possible to acquire an image having a resolving power of a few μm. For example, assuming the wavelength of the low-coherence light M is a Gaussian type and the reflective index of the measured object 1000 is n=1.33, the theoretical value of the resolving power is approximately 1.8 μm.

The image of the measured object 1000 obtained as such is stored in a memory device such as the hard disk drive of the controller 21.

Furthermore, the image forming part 241 can form a 3-dimensional image of the measured object 1000 based on a plurality of tomographic images at different depth-wise positions. The image forming part 241 forms a depth-wise tomographic image based on the 3-dimensional image.

The controller 21 causes the display 22 to display an image of the measured object 1000, for example, in response to an operation of the operation part 23 (operation of designating the depth-wise position) (S9).

For displaying a 3-dimensional image of the measured object 1000, the image forming part 241 applies a known rendering process (volume rendering or MIP (Maximum Intensity Projection)) to the volume data and stack data, thereby forming image data of a pseudo 3-dimensional image of the measured object 1000 taken from a specific viewpoint. The controller 21 causes the display 22 to display the pseudo 3-dimensional image based on this image data.

This is the end of the description of the operation mode of the optical image measurement device 100.

ACTIONS AND ADVANTAGEOUS EFFECTS

The actions and advantageous effects of the optical image measurement device 100 will now be explained.

As described above, the optical image measurement device 100 acts to project the interference light L (polarization components L1 and L2) onto the light receiving face so that the size of the spatial coherent region of the interference light L (polarization components L1 and L2) becomes equal to or larger than the size of the light receiving element on the light receiving face of each of the CCDs 16 and 17.

Figure 5:
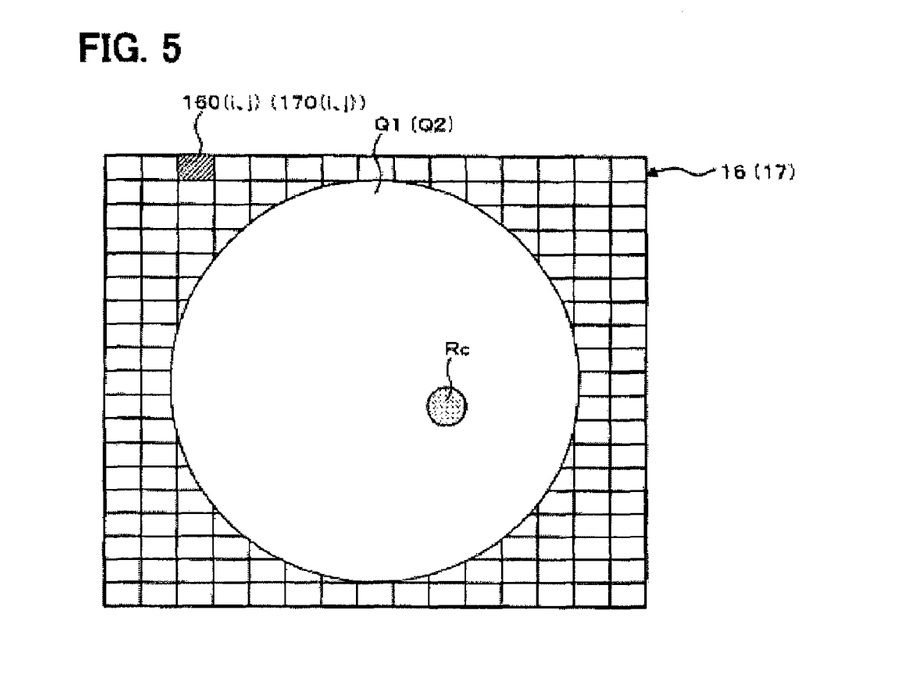
FIG. 5 is a schematic illustration for explaining actions of the embodiment of the optical image measurement device according to the present invention.

The magnitude relation between the spatial coherent region and the light receiving element at this moment is explained with reference to FIG. 5 and FIG. 6. As shown in FIG. 5, a plurality of light receiving elements 160 (i,j) (170 (i,j)) are arranged in a matrix on the light receiving face of the CCD 16 (17). Here, symbols i and j denote that the light receiving elements 160 (i,j) (170 (i,j)) are arranged on the i row and the j column, respectively.

The polarization component L1 (L2) is projected onto the light receiving face of the CCD 16 (17) by the optical system. In FIG. 5, symbol Q1 (Q2) denotes the region (projection region) on the light receiving face where the polarization component L1 (L2) is projected. Symbol Rc denotes the spatial coherent region of the polarization component L1 (L2) on the light receiving face. As shown in FIG. 6, the size of the spatial coherent region Rc is equal to or larger than the size of the light receiving element 160 (i,j) (170 (i,j)).

Accordingly, the light receiving element 160 (i,j) (170 (i,j)) within the projection region Q1 (Q2) receives only the light included in one spatial coherent region Rc substantially. In other words, the light receiving element 160 (i,j) (170 (i,j)) can substantially exclude the light except the one spatial coherent region Rc, and receive the polarization component L1 (L2).

According to the optical image measurement device 100, the interference signal that can be detected by the element—that is, only the interference light included in one spatial coherent region Rc—is projected onto each light receiving element. Therefore, it is possible to efficiently detect the light interference signal. In other words, it is possible to increase the measurement sensitivity. Here, measurement sensitivity means the sensitivity of detection of interference light, such as the ratio of signal and noise (SN ratio) in detection of the interference light. In a charge-accumulating type of sensor like the CCDs 16 and 17, projection of the interference light that does not contribute to detection of interference signals leads to saturation of the sensor. According to the optical image measurement device 100, it becomes possible to exclude unnecessary light projection and, at the same time, obtain high signal values.

Further, according to the optical image measurement device 100, by achieving a spatial coherence as low as the resolution capability of the objective lenses 8 and 11 in the aforementioned manner and projecting the polarization component L1 (L2) onto the CCD 16 (17) so that the size of the spatial coherent region Rc becomes equal to or larger than the size of the light receiving element 160 (i,j) (170 (i,j)), it becomes possible to perform measurement with the same level of resolving power as the objective lenses 8 and 11.

Figure 6:
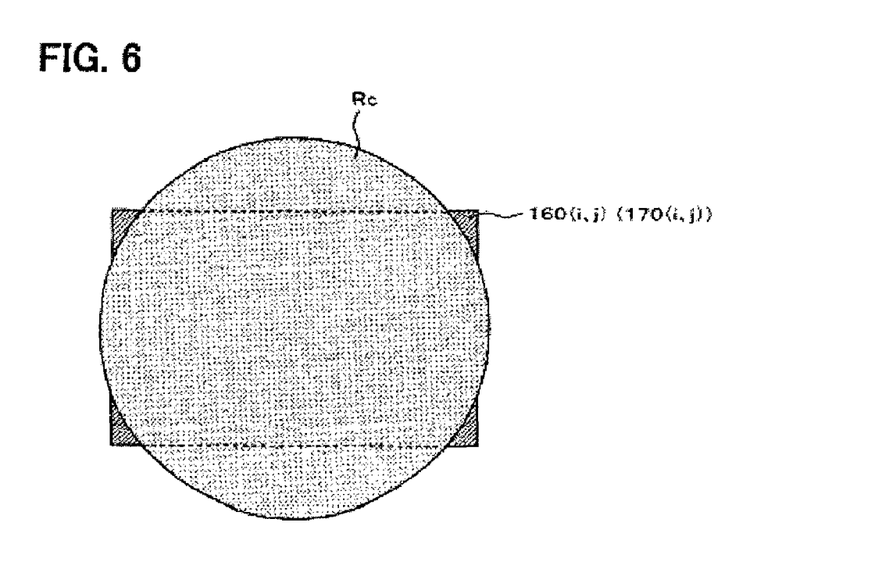
FIG. 6 is a schematic illustration for explaining actions of the embodiment of the optical image measurement device according to the present invention.

For example, as shown in FIG. 6, even if a light other than the spatial coherent region Rc is projected onto a tiny region at the edge of the light receiving element 160 (i,j) (170 (i,j)), as far as an adverse effect thereof on measurement (decrease of the measurement sensitivity) is small, this adverse effect can be ignored.

Further, the optical system of the optical image measurement device 100 is equipped with an aperture member configured to limit the beam diameter of the interference light L. The aforementioned illumination aperture and the aperture 12 are examples of the aperture member. The aperture member may be installed in the optical path of the signal light S or the optical path of the reference light R. In this case, it is desirable to install the aperture members in both the optical paths and control so that the respective aperture values become always equal.

When the aperture value of the aperture member is set, the controller 21 receives the aperture value information that represents this set value. The projection-size determining part 242 obtains the magnification (power) of the variable magnifying lens 18 corresponding to this aperture value information. The controller 21 situates the variable magnifying lens 18 corresponding to the obtained magnification (power) in the optical path of the interference light L. Thus, the size of the spatial coherent region of the interference light L (polarization components L1 and L2) on the light receiving faces of the CCD 16 and 17 is changed.

According to this optical image measurement device 100, the size of the spatial coherent region of the interference light L on the light receiving face can be easily and accurately changed depending on the aperture value of the aperture member for the optical system.

In the abovementioned embodiment, when the size of the spatial coherent region becomes larger than that of the light receiving element, the range of the measured object 1000 to be imaged becomes smaller. For example, in the condition shown in FIG. 5, if the area of the spatial coherent region is doubled, the beam diameter of the polarization component L1 (L2) expands beyond the light receiving face. Therefore, part of the image of the projection region of the signal light S in the measured object 1000 cannot be obtained.

In order to prevent such a problem, it is possible to configure so as to project the interference light (polarization component) onto the light receiving face so that the size of the spatial coherent region of the interference light (polarization component) becomes substantially equal to that of the light receiving element. The "substantially equal" range may be such a small range that an adverse effect on measurement (decrease of the measurement sensitivity) can be ignored.

Also in this configuration, as well as in the abovementioned embodiment, it is desirable to project the interference light (polarization component) onto the light receiving face so that the size of the spatial coherent region becomes equal to or larger than that of the light receiving element. This enables improvement of the measurement sensitivity without narrowing the measurement range (potential imaging range).

Modification

The configuration detailed above is only an example of the preferable embodiment of the present invention. Those who intend to implement the present invention can implement any modification within the scope of the present invention as needed. Such modifications will be explained below.

In the abovementioned embodiment, it is assumed that all the light receiving elements 160 (i,j) (170 (i,j)) of the CCD 16 (17) are the same size. However, this assumption is not necessary in the present invention. In a case where the light receiver includes light receiving elements of different sizes, for example, the interference light may be projected onto the light receiving face so that the size of the spatial coherent region becomes equal to or larger than that of the light receiving element of the maximum size.

A configuration example in a case where the measured object is an eye will now be explained. An eye has a pupil that functions as an aperture. The size of a pupil (pupil diameter) varies depending on peripheral brightness or the like. A change in the pupil diameter is equivalent to that in the aperture value.

The optical image measurement device relating to the modification has the same configuration as in the abovementioned embodiment (see FIG. 1 and FIG. 2). The optical image measurement device receives pupil diameter information of an eye. The pupil diameter information is information representing the pupil diameter of an eye. The pupil diameter is generally used as information that represents the pupil size in the field of opthalmology. Instead of a pupil diameter, any value that represents the pupil size, such as the area and circumferential length of the pupil, can be applied (in the present specification, these values are collectively referred to as the "pupil diameter").

The pupil diameter information is acquired by measuring the diameter of the black part in the image of anterior segment, for example. The anterior segment image may be acquired with another device. The pupil diameter information can be inputted manually, for example, by means of user interfaces (e.g., the abovementioned display 22 and operation part 23). Further, it can be obtained through a communication line such as a LAN. In this case, a communication interface such as a LAN card and a modem is installed in the controller 21. In addition, pupil diameter information recorded in a recording media such as a DVD may be retrieved. In this case, a driver device that retrieves the information recorded in the recording media is installed in the controller 21.

In the same manner as in the aforementioned embodiment regarding the aperture value information, the optical image measurement device obtains the magnification (power) of the variable-magnifying lens based on the pupil diameter information. Then, the optical image measurement device situates the variable magnifying lens with the obtained magnification in the optical path of the interference light, and thereby changes the size of the spatial coherent region of the interference light on the light receiving face of the light receiver. Consequently, the size of the spatial coherent region of the interference light projected onto the light receiving face of the light receiver becomes equal to or larger than that of the light receiving element.

According to this optical image measurement device 100, it is possible to easily and accurately change the size of the spatial coherent region of the interference light on the light receiving face, depending on the pupil diameter of the eye to be examined.

Further, in the same manner as in the abovementioned embodiment, it is possible to configure the optical image measurement device so that the size of the spatial coherent region of the interference light projected onto the light receiving face of the light receiver becomes substantially equal to that of the light receiving elements. This enables improvement of the measurement sensitivity without narrowing a measurement range (potential imaging range).

Also in this modification, as in the abovementioned embodiment, a single variable magnifying lens may be installed, a plurality of variable magnifying lenses with different powers may be installed, or a variable magnifying lens whose power can be continuously changed, may be installed.

The abovementioned embodiment employs a configuration of changing the size of the spatial coherent region of the interference light by using the variable magnifying lens. However, in the present invention, it is also possible to configure so as to change the size of the spatial coherent region by optionally applying other known techniques.

Further, in the present invention, it is not necessary to have a configuration of changing the size of the spatial coherent region. For example, it is possible to fix the conditions (aperture value, magnification, etc.) of various optical elements that compose the optical system, and configure the optical system so that the size of the spatial coherent region of the interference light becomes always equal to or larger than that of the light receiving element on the light receiving face. Moreover, it is also possible to fix the conditions (aperture value, magnification, etc.) of various optical elements that compose the optical system, and configure the optical system so that the size of the spatial coherent region of the interference light becomes always substantially equal to the size of the light receiving elements on the light receiving face.

What is claimed is:

1. An optical image measurement device comprising:
   a light source configured to output a light having low temporal coherence and low spatial coherence;
   a beam splitter configured to split the light into a signal light and a reference light and superimpose the signal light having passed through a measured object and the reference light having passed through a reference object, thereby generating an interference light;
   a changing part configured to change a beam diameter of the interference light projected onto a light receiving face so that a size of a spatial coherent region of the interference light becomes equal to or larger than a size of a light receiving element on the light receiving face;
   a light receiver, having a receiving surface on which a plurality of receiving elements are two-dimensionally arranged, configured to receive the interference light on the receiving surface and output an electric signal; and
   a forming part configured to form an image of the measured object based on the electric signal.

2. The optical image measurement device according to claim 1, wherein:
   the changing part includes an aperture member configured to limit a beam diameter of the interference light, and a variable magnifying lens provided so that it can be situated in an optical path of the interference light,
   the optical image measurement device further comprising:
   a controller configured to receive aperture value information of the aperture member, determine such a magnification that the size of the spatial coherent region becomes equal to or larger than the size of the light receiving element based on the aperture value information, and situate the variable magnifying lens in the optical path based on the determined magnification.

3. The optical image measurement device according to claim 2, wherein:
   the changing part includes a plurality of variable magnifying lenses with different magnifications; and
   the controller selects a variable magnifying lens corresponding to the determined magnification from among the plurality of variable magnifying lenses, and situates it in the optical path.

4. The optical image measurement device according to claim 1, wherein:
   the measured object is an eye; and
   the changing part includes a variable magnifying lens provided so that it can be situated in an optical path of the interference light,
   the optical image measurement device further comprising:
   a controller configured to receive pupil diameter information of the eye, determine such a magnification that the size of the spatial coherent region becomes equal to or larger than the size of the light receiving element based on the pupil diameter information, and situate the variable magnifying lens in the optical path based on the determined magnification.

5. The optical image measurement device according to claim 4, wherein:
   the changing part includes a plurality of variable magnifying lenses with different magnifications; and
   the controller selects a variable magnifying lens corresponding to the determined magnification from among the plurality of variable magnifying lenses, and situates it in the optical path.

6. The optical image measurement device according to claim 1, wherein: the light source is a heat light source.

7. The optical image measurement device according to claim 1, wherein:
   the beam splitter optical system includes a moving part configured to situate the reference object in a first position and a second position, and a splitter configured to split the interference light into a P polarization component and an S polarization component;
   the light receiver includes a pair of light receivers configured to receive the P polarization component and the S polarization component, respectively; and
   the forming part forms a tomographic image of the measured object in a cross section orthogonal to a travel direction of the signal light S projected onto the measured object, based on a pair of electric signals according to the P polarization component and the S polarization component received by the pair of light receivers when the reference object is situated in the first position, and a pair of electric signals according to the P polarization component and the S polarization component received by the pair of light receivers when the reference object is situated in the second position.

8. An optical image measurement device comprising:
   a light source configured to output a light having low temporal coherence and low spatial coherence;
   a beam splitter configured to split the light into a signal light and a reference light and superimpose the signal light having passed through a measured object and the reference light having passed through a reference object, thereby generating an interference light;

a changing part configured to change a beam diameter of the interference light projected onto a light receiving face so that a size of a spatial coherent region of the interference light becomes substantially equal to a size of the light receiving element on the light receiving face;

a light receiver, having a receiving surface on which a plurality of receiving elements are two-dimensionally arranged, configured to receive the interference light on the receiving surface and output an electric signal; and a forming part configured to form an image of the measured object based on the electric signal.

9. The optical image measurement device according to claim 8, wherein:

the changing part includes an aperture member configured to limit a beam diameter of the interference light, and a variable magnifying lens provided so that it can be situated in an optical path of the interference light, the optical image measurement device further comprising:

a controller configured to receive aperture value information of the aperture member, determine such a magnification that the size of the spatial coherent region becomes substantially equal to the size of the light receiving element based on the aperture value information, and situate the variable magnifying lens in the optical path based on the determined magnification.

10. The optical image measurement device according to claim 9, wherein:

the changing part includes a plurality of variable magnifying lenses with different magnifications; and the controller selects a variable magnifying lens corresponding to the determined magnification from among the plurality of variable magnifying lenses, and situates it in the optical path.

11. The optical image measurement device according to claim 8, wherein:

the measured object is an eye; and the changing part includes a variable magnifying lens provided so that it can be situated in an optical path of the interference light, the optical image measurement device further comprising:

a controller configured to receive pupil diameter information of the eye, determine such a magnification that the size of the spatial coherent region becomes substantially equal to the size of the light receiving element based on the pupil diameter information, and situate the variable magnifying lens in the optical path based on the determined magnification.

12. The optical image measurement device according to claim 11, wherein:

the changing part includes a plurality of variable magnifying lenses with different magnifications; and the controller selects a variable magnifying lens corresponding to the determined magnification from among the plurality of variable magnifying lenses, and situates it in the optical path.

13. The optical image measurement device according to claim 8, wherein:

the light source is a heat light source.

14. The optical image measurement device according to claim 8, wherein:

the beam splitter includes a moving part configured to situate the reference object in a first position and a second position, and a splitter configured to split the interference light into a P polarization component and an S polarization component;

the light receiver includes a pair of light receivers configured to receive the P polarization component and the S polarization component, respectively; and the forming part forms a tomographic image of the measured object in a cross section orthogonal to a travel direction of the signal light projected onto the measured object, based on a pair of electric signals according to the P polarization component and the S polarization component received by the pair of light receivers when the reference object is situated in the first position, and a pair of electric signals according to the P polarization component and the S polarization component received by the pair of light receivers when the reference object is situated in the second position.

* * * * *